United States Patent [19]

Friese

[11] 4,296,148
[45] Oct. 20, 1981

[54] METHOD TO APPLY MULTIPLE LAYERS, INCLUDING AN ELECTRODE LAYER, ON A SINTERED OR PRE-SINTERED ION CONDUCTIVE SOLID ELECTROLYTE BODY

[75] Inventor: Karl-Hermann Friese, Leonberg, Fed. Rep. of Germany

[73] Assignee: Robert Bosch GmbH, Stuttgart, Fed. Rep. of Germany

[21] Appl. No.: 98,602

[22] Filed: Nov. 29, 1979

[30] Foreign Application Priority Data

Dec. 6, 1978 [DE] Fed. Rep. of Germany ....... 2852647

[51] Int. Cl.³ .............................................. B05D 5/12
[52] U.S. Cl. .................................. 427/125; 427/123; 427/126.2; 427/126.4; 427/126.5; 427/261; 427/269; 427/376.1; 427/376.2; 427/376.3; 427/376.6; 427/419.3; 204/195 S
[58] Field of Search ..................... 204/195 S; 427/125, 427/126.2, 126.4, 126.5, 261, 269, 376.1, 376.2, 376.3, 376.6, 419.3, 123

[56] References Cited

U.S. PATENT DOCUMENTS

| | | | |
|---|---|---|---|
| 3,347,767 | 10/1967 | Hickam | 204/195 S |
| 3,503,809 | 3/1970 | Spacil | 204/195 S |
| 3,645,875 | 2/1972 | Record et al. | 204/195 S |
| 3,843,400 | 11/1974 | Radford et al. | 429/152 |
| 3,935,089 | 1/1976 | Togawa et al. | 204/195 S |
| 3,978,006 | 8/1976 | Topp et al. | 204/195 S |
| 4,005,001 | 1/1977 | Pebler | 324/425 |
| 4,021,326 | 5/1977 | Pollner et al. | 204/195 S |
| 4,096,648 | 6/1978 | Matsumoto et al. | 204/195 S |

Primary Examiner—Ronald H. Smith
Assistant Examiner—Richard Bueker
Attorney, Agent, or Firm—Frishauf, Holtz, Goodman & Woodward

[57] ABSTRACT

To improve response time and provide an electrode which has good adhesion to a solid electrolyte body, typically of zirconium, to be used in lambda sensors or polarographic current limit sensors, and additionally enhance the loading capability thereof, the pre-sintered or fully sintered solid electrolyte body, typically of zirconium dioxide, has an electrode layer applied thereto on which, in advance of sintering thereof, a cover layer is applied which, when sintered, develops pores. The cover layer is a ceramic material, sintered together with the electrode on the solid electrode body. This results in higher loading capability and decrease in response temperature to about 250° C. The sensors can be used as lambda sensors and polarographic current sensors, to determine oxygen content in exhaust gases, typically for automotive engines, as well as in high-temperature fuel cells, high-temperature batteries, and high-temperature electrolysis cells.

24 Claims, 1 Drawing Figure

U.S. Patent  Oct. 20, 1981  4,296,148
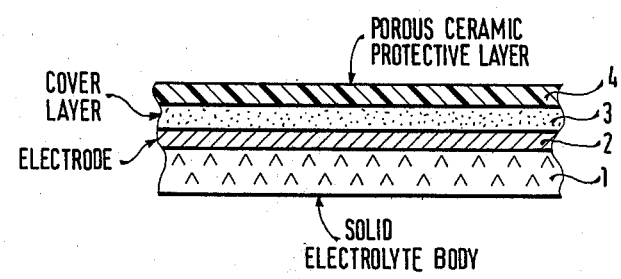

METHOD TO APPLY MULTIPLE LAYERS, INCLUDING AN ELECTRODE LAYER, ON A SINTERED OR PRE-SINTERED ION CONDUCTIVE SOLID ELECTROLYTE BODY

Reference to related patents and applications, assigned to the assignee of the present application:

U.S. Pat. No. 3,798,006, TOPP and FRIESE;

German Disclosure Document No. 28 10 134 to which U.S. Pat. No. 4,221,650, Friese et al corresponds;

U.S. Ser. No. 06/098 708, filed Nov. 9, 1979, Haecker et al;

U.S. Ser. No. 100,256, filed Dec. 4, 1979, MAURER et al.

The present invention relates to a method to apply multiple layers, and particularly electrode layers to an ion conductive solid electrolyte body, for example of the type used in gas sensors, typically to sense the composition of exhaust gases from internal combustion engines. The solid electrolyte body may, for example, be zirconium dioxide.

BACKGROUND AND PRIOR ART

Multiple layers, including electrode layers, have to be applied to support structures, such as plate or tubular sensing elements made of an ion conductive solid electrolyte in order to utilize the characteristic of the electrolyte to determine the gas composition, typically the composition of exhaust gases resulting from combustion processes, for example the exhaust gases from internal combustion engines, and especially to determine the oxygen content therein. Such sensors, referred to also as lambda sensors, and which provide output voltages which change in dependence on the composition of a test gas with respect to a reference gas, usually are so made that a pre-sintered solid electrolyte body has an electrode layer applied thereto which is then sintered on the body. The surface of the body, with the electrode layer thereon which is exposed to the exhaust gas is then covered with a ceramic cover coating which is porous and which, once more, is sintered or which is plasma-sprayed only. The electrode at the opposite surface of the body, for example at the interior of a tubular structure, and which is normally exposed to a reference gas, for example ambient air, has an electrode applied thereto, but usually does not have a protective cover layer applied thereover.

It has been found that the electrodes of such sensors cannot be sufficiently loaded with electrical current, that is, the level of current loading was not adequate. This is particularly applicable with respect to the inner electrodes of tubular bodies. The electrical loading is particularly important during the start-up phase of operation of such sensors. The sensors, preferably, should be so constructed or formed that they will be fully operable at a temperature of already 300° C. As the temperature drops, the $O^{2-}$ ion conductivity of customary solid electrolyte material drops rapidly, that is, the inner or interior inherent resistance of the sensor increases correspondingly. If high electrode polarization is added by electrodes which can be loaded only inadequately, the sensor can operate reliably and free from disturbances only at higher temperatures unless expensive and complex evaluation electronic systems are used in connection therewith.

THE INVENTION

It is an object to improve the electrode system on solid electrolyte bodies, and particularly to provide electrode systems which have good adhesion on the underlying body while additionally permitting high current loading thereof.

Briefly, a layer of electrode material, such as a platinum layer, for example in paste form, is applied on the electrode body which already is sintered or pre-sintered. Before sintering the electrode layer, a ceramic material layer is applied over the electrode layer; the electrode layer and the ceramic cover layer are then sintered to form a porous cover layer of ceramic material and the electrode in one step. Thus, the step of applying the cover layer over the electrode is carried out in advance of heating of the electrode layer to a temperature at which sintering process in the electrode layer material may commence, the composite layers being sintered thereafter.

The method has the advantage that electrode systems can be formed on solid electrolyte bodies or base structures for electrochemical sensing use which, besides excellent adhesion on the solid electrolyte body, exhibit high electrical loading capability. When used in the lambda sensors, the start-up temperature is decreased with respect to sensors made by other processes.

It has been found in the usual electrodes previously made that the surface layer tended to coagulate or to grain growth of the electron conductive particles during treatment steps applied to the electrode layers after their initial application to the support structure, i.e. the solid electrolyte body. It appears that this coagulation or grain growth of the electron conductive particles had the effect of decreasing current carrying capacity and requiring higher start-up temperatures. This effect appears to be suppressed when the cover layer is applied to the electrode surface during the sintering process. In the customary electrodes which contain precious metal, for example platinum electrodes, the cover layers may consist, for example, of $Al_2O_3$ or $ZrO_2$, or mixtures thereof.

In accordance with a feature of the invention, the electrode need not be platinum but may be an oxide-type electrode material. The advantages of the present invention are also applicable if the electrode is an oxide-type material. The cover layer and the electrode together require only a final thermal treatment. Thus, it is not necessary in the process that the solid electrolyte body also is being sintered. Rather, one can start from a fully sintered base solid electrolyte body. It is thus possible, in accordance with a feature of the invention, to use Perovskite electrodes, for example, that is, electrodes with doped $LaCoO_3$ in porous form which can be sintered on the solid electrolyte body to have excellent adhesion, without impairing the functional or operational characteristics of such electrodes if they are covered subsequently with a layer consisting, for example, of titanium dioxide, a titanium dioxide-aluminum oxide mixture, or aluminum oxide, and the final sintering is carried out only thereafter. Sintering can be carried out at elevated temperatures, which leads to better adhesion of the electrode on the solid electrolyte body without in any way impairing the load carrying capacity or loading capability of the electrode.

In accordance with a particularly advantageous feature of the invention, the electrodes may be cermet electrodes. Cermet electrodes consist of a mixture of platinum metal powder and a ceramic powder. In such electrodes, the additional advantage is obtained that the stabilization of the thermodynamic equilibrium at a three-phase boundary of the electrode is substantially accelerated, particularly upon sudden changes of the gas composition to which the sensor is exposed.

Drawing, illustrating an example, wherein the single FIGURE is a highly schematic fragmentary cross-sectional view through an electrode layer on a solid electrolyte body which, overall, may be in tubular form, for example.

The method, when carried out, results in application of an electrode 2 on a solid electrolyte body 1, the electrode tube being covered with a cover layer 3. The drawing illustrates a boundary line between the cover layer and the electrode. This is schematic only, and this boundary may, actually, not be present as a clearly defined boundary but, rather, be a diffuse or interlaced zone of electrode material and the material of the cover layer 3, sintered on the solid electrolyte body 1.

The porous cover layer 3, preferably, is made in this manner: Suitable materials which, by a sintering process, can be changed by solid-state reaction to the desired material, are applied on the not-yet-sintered electrode layer 2 which, in turn, has been applied to a sintered or pre-sintered solid electrolyte body.

The cover layer may, for example, consist of CaO stabilized $ZrO_2$, a mixture of $ZrO_2$ a suitable corresponding quantity of $CaCO_3$, or a mixture of $Zr(CO_3)_2$ and a corresponding quantity $CaCO_3$. The selected, respective material is applied on the electrode layer 2 which is not yet sintered. If the cover layer is to consist of magnesium spinel, a mixture of $MgCO_3$ and $Al_2O_3$ in appropriate relationship can be applied to the electrode layer.

The porous cover layer further, and preferably, can be so made that the ceramic material is applied in a modification which is unstable at sintering temperature, for example aluminum oxide in the form of $\gamma$—$Al_2O_3$, titanium dioxide of anatas, or zirconium dioxide in the form of monocline $ZrO_2$. Upon sintering, the corresponding high temperature forms will result by phase conversion. Phase conversion favors the effect of the cover layer with respect to loadability of the electrodes.

If necessary, the electrode layer, together with the cover layer which is to be sintered, can have a further porous ceramic layer 4 applied thereto, for example as a protective layer. Such a protective layer may be a magnesium spinel layer made by plasma spraying, or a diffusion layer in a current limiting sensor, utilizing a porous ceramic plate or disk which is applied to the surface of cover layer 3.

The advantages of the method are available for sensors operating both as lambda sensors, that is, sensors which exhibit a sharp transition voltage output upon change of a gas to which the surface opposite layer 4, for example, is exposed with respect to the oxygen content of a reference gas, to which the lower surface of solid electrolyte body 1 is exposed, and also with respect to polarographic or current limiting sensors. Polarographic sensors are sensors which operate within the range of the diffusion limiting current and, normally, have voltages applied thereto. The method results in better current limiting curves and operability at lower operating temperatures. Additionally, the method of making the sensor structure is simplified since the method lends itself to using screen printing technology, which is an effective and simple way of applying the various layers 2, 3 and 4—if used—on the body 1.

Example 1, to make a lambda sensor in the form of a tube closed at one end and having a solid electrolyte body 1, utilizing zirconium dioxide ceramic as the structural base:

The solid electrolyte tube is made, in known manner, of a zirconium dioxide ceramic body, fully or partially stabilized with yttrium oxide, and pre-sintered for 2 hours at 1050° C. The outer surface of the closed tube, which is exposed to the exhaust gases, typically from an internal combustion engine, as well as the inner surface which is exposed to a reference gas, typically ambient air, have platinum cermet electrodes applied thereto by spraying or brushing.

The platinum cermet electrodes consist of 60% platinum powder and 40% finely stabilized zirconium dioxide powder—both percentages by volume. The solid electrolyte tube, with the so applied electrodes, is then dried or exposed to glow temperature, for 2 hours at 900° C. The two electrodes are then coated with an aqueous aluminum oxide slick. The slick may, for example, consist of pre-milled, sinter-active alumina with a small percentage of a binder, for example 2% by weight, with respect to the solid material components, of polyvinylacohol. The outer electrode can be coated, for example, by spraying the slick on the surface or by dipping the solid electrolyte body, with the electrode applied, into the slick. The inner electrode is preferably coated by spraying the slick into the tube, or by filling the tube with the slick and then turning the tube over to pour out the slick, leaving a coating on the surface of the body and over the electrode, where the electrode is applied to the body.

After drying of the slick, the solid electrolyte tube with the layers thereon is sintered. If the solid electrolyte ceramic is fully stabilized, a suitable sintering temperature is 1500° to 1650° C. If the solid electrolyte ceramic is partially stabilized, sintering is carried out at 1400° to 1600° C.

Specific examples:

Example 2: Solid electrolyte body with a ceramic consisting of 70% by weight) $ZrO_2$ stabilized with 7.5 mol-% $Y_2O_3$ and 30% (by weight) $Al_2O_3$.

Cermet electrode: 60% (by volume) platinum and 40% $ZrO_2$ powder stabilized with CaO.

Cover coating or layer: $ZrO_2$ powder having at least 99% $ZrO_2$, with a specific surface of at least 10 m$^2$/g.

Sintering: 5 hours at 1550° C.

$ZrO_2$, at a higher sintering temperature, gives a better pore structure than pure $Al_2O_3$.

Example 3: Solid electrolyte and cermet electrode as in Example 2. Cover coating or layer: 75% $ZrO_2$ powder (by weight) as in Example 2. 25% (by weight) $Al_2O_3$ powder, with a specific surface of about 10$^2$ m/g.

This embodiment has better adhesion with respect to that of Example 2.

Example 4: Solid electrolyte ceramic and cermet electrode as in Example 2.

Cover coating or layer for the outer electrode: 90% (by weight) $ZrO_2/Al_2O_3$ mixture as in Example 3 and 10% (by weight) platinum powder.

The cover layer is activated by the presence of platinum which improves the establishment of thermodynamic equilibrium of the exhaust gases to which the outer surface of the body is exposed at the three-phase boundary of the sensor.

The improvement of the sensor obtained by the method of the invention is best shown by listing the results of measurements of polarization of a lambda sensor with and without a cover layer, and loading of the sensor with a parallel resistor of 100 kΩ. The base structure of the sensor was as follows:

Example 5: Solid electrolyte body: $ZrO_2$ partially stabilized with $Y_2O_3$.

Cermet electrodes, by volume, 60% Pt/40% $ZrO_2$, fully stabilized with $Y_2O_3$.

Sintering: 1500° C., 30 minutes.

Shape of sensor: Tubular, closed at one end.

Reference gas, applied to the inner bore of the sensor: ambient air.

Measuring temperature: 350° C.

Test gas: Combustion exhaust gas of a propane burner, λ<1; 1% CO.

Thickness of the cover layers: Outer electrode: 15–30 μm. Inner electrode: 25–50 μm.

The polarization voltages with different cover layers are reproduced on the Table, forming part of this specification.

The table clearly shows that sensors which are made by the process of the present invention, and which carry a porous cover layer on the electrodes and which are sintered together with the electrodes, have a marked decrease of polarization, so that they will accept higher electrical loading and have a lower start-up or initial operating temperature.

Generally, the volumetric ratio of the electrically conductive material to ceramic material of the electrode, which is customarily applied in paste form, should be above about 1:4. If the electrode layer itself is a semiconductive ceramic material, such as Perovskite which essentially consists of: e.g. doped Co-La-oxide, then it may be pre-dried of slightly pre-sintered before the cover layer or cover coating is applied thereto for final sintering thereafter. The temperature range of this pre-sintering, of course, should be substantially below the final sintering temperature. The porous cover layer preferably consists of aluminum oxide, magnesium spinel, stabilized zirconium dioxide, pure zirconium dioxide, zirconium silicate, or titanium dioxide, singly or in mixtures. Particularly preferred cover layers are given in the examples. The porous cover layer can be applied either in the form of a material which will remain the same after sintering or which, only during the subsequent sintering process, will transform or convert into the desired material by solid-state reaction. Two particularly suitable cover layers are $ZrO_2$ stabilized with CaO, which is obtained from an initial mixture of $ZrO_2$ and $CaCO_3$, or a cover layer of magnesium spinel, obtained from an initial mixture of $MgCO_3$ and $Al_2O_3$. The ceramic material initially applied may be unstable at the sintering temperature which, at the subsequent sintering process, by phase transformation, will transform into the high temperature structure. A suitable material is aluminum oxide in the form of $\gamma$—$Al_2O_3$, titanium dioxide in the form of anatas, or zirconium dioxide in the form of monocline $ZrO_2$. The porous structure of the porous cover layer can be enhanced by adding a pore-enhancing substance, for example 20% by volume of thermally obtained carbon black, or ammonium carbonate or by adding microspheres of organic materials.

A further porous ceramic cover layer can be applied after the electrode and first cover layer have been applied and have been sintered; such a further porous cover layer suitably may be magnesium spinel, applied by plasma spraying. The further porous ceramic cover layer 4 may be catalytically active, by suitable addition of a catalytic material, for example admixing about 0.1 to 10% (by volume) of a noble metal powder, for example platinum. Either or both of the ceramic cover layers, that is, the cover layer directly on the electrode or the further cover layer may be so activated to provide catalytic activity therefor. Pore-forming additives may be used with the materials for cover layers 3 and/or 4, e.g. carbon black or ammonium carbonate, present in about 20% by volume or in the form of microspheres of organic materials.

The sensors can be used as lambda sensors and polarographic current sensors, to determine oxygen content in exhaust gases, typically for automotive engines, as well as in high-temperature fuel cells, high-temperature batteries, and high-temperature electrolysis cells.

TABLE

| Cover layers | | |
|---|---|---|
| Reference (inner) electrode | Exhaust (outer) electrode | Polarization ΔU (mV) |
| $\alpha$—$Al_2O_3$ (~10 m²/g) | $\alpha$—$Al_2O_3$ (~10 m²/g) | 280 ± 25 |
| 90% by weight $ZrO_2$/ 10% by weight CaO (grain size: 2–10 μm) | $\alpha$—$Al_2O_3$ (~10 m²/g) | 285 ± 20 |
| none | $\alpha$—$Al_2O_3$ (~10 m²/g) | 365 ± 15 |
| none | none | 425 ± 30 |

I claim:

1. Method of making a solid electrolyte ion conductive gas sensing element having
   a solid ion conductive electrolyte body (1) having two surface portions, one of which is adapted for exposure to the gas to be sensed
   a layer of electrode material (2) on one surface portion of the body;
   a layer of electrode material on the second surface portion of the body;
   a cover layer of porous ceramic material on the layer of electrode material on said one surface portion of the body; and
   a cover layer of porous ceramic material on the layer of electrode material on said second surface portion of the body,
   comprising the steps of
   providing a pre-sintered ion conductive solid electrolyte body having said two surface portions,
   applying a layer of the electrode material on one surface portion of said body;
   applying a layer of the electrode material on the second surface portion of said body;
   applying a cover layer of ceramic material which, when sintered, becomes porous, on the layer of electrode material on one surface portion of said body;
   applying a cover layer of ceramic material which, when sintered, becomes porous on the layer of electrode material on the second surface portion of said body; and
   then in one step, sintering the electrode layers and the cover layers, by heating the body with the electrode layers and the cover layers applied thereon to a temperature in which the sintering process of the electrode layers at least commences and the ion conductive body and the cover layer are completely sintered.

2. Method according to claim 1, wherein the electrode layers comprise a paste including finely dispersed ceramic material and finely dispersed electrically conductive material;
the paste is dried after applying the paste forming the electron conductive layer on the solid electrolyte body; and
the cover layers are applied in the form of a ceramic slip, the composite of the ion conductive body with the paste and slip thereover applied thereto being sintered thereafter.

3. Method according to claim 2, wherein the volumetric relationship of the electrically conductive material to ceramic material in the paste which forms the electron conductive layers is above about 1:4.

4. Method according to claim 1, wherein the porous cover layers comprise at least one of the materials selected from the group consisting of: aluminum oxide, magnesium spinel, stabilized zirconium dioxide, pure zirconium dioxide, zirconium silicate, titanium dioxide, singly or in mixtures.

5. Method according to claim 4, wherein
the material being applied over the electrode layers, before sintering, comprises a material which changes upon sintering by solid-state reaction to form the porous cover layers.

6. Method according to claim 5, wherein the material being applied to the electrode layers comprises a mixture of $ZrO_2$ and $CaCO_3$ to form, upon sintering, by solid-state reaction $ZrO_2$ stabilized by CaO.

7. Method according to claim 5, wherein the material being applied to the electrode layers comprises a mixture of: $MgCO_3$ and $Al_2O_3$ to form, upon sintering by solid-state reaction, cover layers of magnesium spinel.

8. Method according to claim 4, wherein the material of the cover layers is a ceramic material which is in unstable form and which, during the subsequent sintering step, is transformed into the high temperature form by phase change.

9. Method according to claim 8, wherein the material applied to the electrode layers comprises at least one of the materials selected from the group consisting of: aluminum oxide in the form of $\gamma-Al_2O_3$, titanium dioxide in the form of anatas, or zirconium dioxide in the form of monocline $ZrO_2$.

10. Method according to claim 4, including a pore-forming additive added to the material forming the cover layers.

11. Method according to claim 10, wherein the pore-forming additive comprises carbon black or ammonium carbonate, present in about 20% by volume or microspheres of organic materials.

12. Method according to claim 1, further comprising the step of applying further respective porous ceramic cover layers over said cover layers of ceramic material after the sintering step.

13. Method according to claim 12, wherein said further cover layers comprise magnesium spinel applied by plasma spraying.

14. Method according to claim 1, including the step of catalytically activating said cover layers of ceramic material.

15. Method according to claim 12, including the step of catalytically activating at least one of said cover layers.

16. Method according to claim 14, wherein the step of catalytically activating the respective cover layer comprises the step of adding a noble metal powder in a quantity of between about 0.1 to 10% (by volume) to the ceramic material forming the cover layer.

17. Method according to claim 15, wherein the step of catalytically activating the at least one cover layer comprises the step of adding a noble metal powder in a quantity of between about 0.1 to 10% (by volume) to the ceramic material forming said at least one cover layer.

18. Method according to claim 1, wherein the material of the layers of electrode material comprises a semiconductive ceramic material; and
further including the step of heating said semiconductive ceramic material to a temperature below sintering temperature, then applying the cover layers of ceramic material and then conjointly sintering the electrode layers and the cover layer.

19. Method according to claim 18, wherein the semiconductive ceramic electrode material comprises Perovskite.

20. Method according to claim 1 or 2 or 3 or 10 wherein the pre-sintered ion conductive body comprises partially stabilized zirconium dioxide; and
said single sintering step comprises heating the pre-sintered ion conductive solid electrolyte body with the electrode layers and the cover layers applied thereon to a temperature of between about 1,500° C. to 1,650° C.

21. Method according to claim 1, 2 or 3 or 10 wherein the presintered ion conductive body comprises fully stabilized zirconium dioxide; and
the single sintering step comprises heating the presintered ion conductive solid electrolyte body, with the electrode layers and the cover layers applied thereon to a temperature of between about 1,400°–1,600° C.

22. Method according to claim 1, 2 or 3, or 10 wherein the presintered ion conductive body comprises zirconium dioxide, and the single sintering step comprises heating the presintered ion conductive solid electrolyte body, with the electrode layers and the cover layers applied thereon to a temperature of about 1,550° C. for a period of about 5 hours.

23. Method according to claim 21 wherein the single sintering step comprises heating for a period of about ½ hour to a temperature of about 1,500° C.

24. Method according to claim 1 wherein said single sintering step comprises heating the pre-sintered ion conductive solid electrolyte body with the electrode layers and the cover layers applied thereon to a temperature at which the electrode layers, the ion conductive body, and the cover layer are completely sintered together.

* * * * *